(12) United States Patent
Worden

(10) Patent No.: US 7,065,401 B2
(45) Date of Patent: Jun. 20, 2006

(54) METHOD OF APPLYING ELECTRICAL SIGNALS TO A PATIENT AND AUTOMATIC WEARABLE EXTERNAL DEFIBRILLATOR

(76) Inventor: Michael Worden, c/o Cardiac Science, Inc., 5420 Feltl Rd., Minneapolis, MN (US) 55343

( * ) Notice: Subject to any disclaimer, the term of this patent is extended or adjusted under 35 U.S.C. 154(b) by 480 days.

(21) Appl. No.: 10/431,348

(22) Filed: May 7, 2003

(65) Prior Publication Data

US 2003/0216787 A1    Nov. 20, 2003

Related U.S. Application Data

(60) Provisional application No. 60/378,921, filed on May 8, 2002.

(51) Int. Cl.
*A61N 1/04* (2006.01)

(52) U.S. Cl. .................. 607/5; 607/2; 607/115; 607/142

(58) Field of Classification Search ............ 607/2, 607/5, 7, 115, 129, 142, 148, 152
See application file for complete search history.

(56) References Cited

U.S. PATENT DOCUMENTS

| | | | |
|---|---|---|---|
| 5,405,361 | A | 4/1995 | Persson |
| 5,643,324 | A | 7/1997 | Persson |
| 5,697,955 | A | 12/1997 | Stolte |
| 6,115,638 | A | 9/2000 | Groenke |
| 6,280,461 | B1 | 8/2001 | Glegyak et al. |
| 6,289,243 | B1 | 9/2001 | Lin et al. |
| 6,480,734 | B1 | 11/2002 | Zhang et al. |
| 6,490,478 | B1 | 12/2002 | Zhang et al. |
| 6,546,285 | B1 | 4/2003 | Owen et al. |
| 2002/0107553 | A1 | 8/2002 | Hill et al. |
| 2003/0023277 | A1 | 1/2003 | Owen et al. |

*Primary Examiner*—Robert E. Pezzuto
*Assistant Examiner*—Brian T. Gedeon
(74) *Attorney, Agent, or Firm*—Patterson, Thuente, Skaar & Christensen, P.A.

(57) ABSTRACT

A system, apparatus, and method of delivering a defibrillation pulse to the heart of a patient generally includes positioning a pair of electrodes on the exterior surface of the patient's body such that at least one of the electrodes is placed on a limb, e.g., arm or leg, of the patient in a position proximate to the patient's torso. An electrical defibrillation pulse is then delivered through the electrodes, into the limb, enabling the electrical defibrillation pulse to travel from the limb to the heart of the patient.

16 Claims, 5 Drawing Sheets

METHOD OF APPLYING ELECTRICAL SIGNALS TO A PATIENT AND AUTOMATIC WEARABLE EXTERNAL DEFIBRILLATOR

RELATED APPLICATIONS

The present application claims the benefit of U.S. Provisional Application No. 60/378,921, filed May 8, 2002, and herein incorporated by reference in its entirety.

FIELD OF THE INVENTION

This invention relates to a method of applying electrical signals to the human body to halt sudden cardiac arrest. More particularly, the present invention relates to methods and apparatus for applying electrical defibrillation pulses to the limbs of a patient proximate their torso such that at least a portion of the electrical defibrillation pulse is delivered to the heart through the arterial or veinous systems.

BACKGROUND OF THE INVENTION

Sudden Cardiac Arrest (SCA) is one of the leading causes of death in the United States. Each year, it is estimated that over 450,000 Americans die from SCA. SCA occurs when the heart stops beating normally and is no longer able to effectively pump oxygenated blood to the brain and other vital organs. When a person experiences SCA, delivery of treatment as quickly as possible is critical as death can occur within minutes. Currently, the only known effective treatment to halt SCA is prompt external or internal defibrillation.

External defibrillation is a treatment process in which an electrical waveform, hereafter referred to as an electrical defibrillation pulse, is applied to the cardiac muscle resulting in the cessation of rapid uncoordinated contractions of the heart. Following external defibrillation, the heart is restored to its normal beating state. External defibrillation treatment is commonly administered with an automated external defibrillator that includes heart rhythm sensors, current generating circuitry and electrode pads for delivering the electrical defibrillation pulse. Automated external defibrillators are available in a variety of configurations including varieties frequently seen in hospitals or on television as well as the smaller, more portable models frequently found in airplanes, shopping malls, stadiums and nursing homes.

Using the heart rhythm sensors, the automated external defibrillator is able to determine whether a person is actually suffering from SCA and if electrical defibrillation is required. If the sensors determine that electrical defibrillation is necessary, the current generating circuitry discharges, delivering the electrical defibrillation pulse through the electrode pads which are positioned over the chest area of the person.

Due to the size and density of the chest cavity, it is estimated that only 4% of the current delivered by the automated external defibrillator actually reaches the heart. This ability of the chest cavity to impede the flow of electrical current is known as transthoracic impedance. Transthoracic impedance is created by the combination of air present in the lungs, fat tissue, muscle tissue, breast tissue, skin, bones and body hair. Due to this transthoracic impedance, automated external defibrillators are typically designed to deliver electrical defibrillation pulses having energy levels of 350–400 Joules such that the heart actually experiences energy levels of between 10–50 Joules.

While the current designs of automated external defibrillators perform excellently with respect to treating SCA, it would be desirable to have an automated external defibrillator design which would eliminate the tremendous current losses inflicted by transthoracic impedance. Such a design would result in an automated external defibrillator that is both more efficient and consequently less expensive to manufacture.

SUMMARY OF THE INVENTION

The automated external defibrillator of the present invention overcomes the current loss problems created by transthoracic impedance by selectively placing at least one of a pair of electrode pads proximate the torso, preferably on a limb of a person experiencing SCA. By placing at least one of the electrode pads on a limb proximate the torso, the electrical defibrillation pulse is delivered at least partially through the arterial or veinous system such that the factors creating transthoracic impedance are avoided and the actual transthoracic impedance encountered is notably reduced in comparison to typical electrode orientation over the chest region.

Generally, the present invention is practiced by securely attaching at least one readily attachable/detachable electrode to a limb of a patient proximate the torso. The second electrode is then positioned over either the chest region or on another limb proximate the torso. Once both electrodes are positioned, an electrical defibrillation pulse is generated by a discharge circuit. Through the aforementioned positioning, at least a portion of such electrical defibrillation pulse is transmitted to the cardiac muscle through either the arterial or veinous systems. The present invention can be practiced with defibrillators of varying configurations such as generally immobile devices configured for hospital and emergency room use, smaller, more mobile devices configured for use in airplanes, nursing homes and sports stadiums as well as wearable and ambulatory style devices for persons especially susceptible to experiencing Sudden Cardiac Arrest.

In an embodiment of the present invention, at least one adjustably securable strap is used to position at least one electrode on a limb proximate the torso of a patient. The adjustably securable strap can include an electrode on an inside surface of the strap and may include additional components, for example, a discharge circuit and a heart monitor circuit. The adjustably securable strap can be designed for positioning on the upper arm or upper leg of a patient. A second electrode can take the form of a second adjustably securable strap over another limb proximate the torso or a stick-on style electrode positioned over the chest region or on a limb proximate the torso. The adjustably securable strap can also include interface means for working with remotely located discharge circuits or heart monitors.

In another embodiment of the present invention, the electrodes of the present invention can take the form of paddles frequently used in hospital or ambulatory situations. Generally, at least one of such paddles would be positioned on a limb proximate the torso of a patient while a second paddle is located either on another limb proximate the torso or over a chest region of the patient.

In some embodiments, the armband may also include a housing containing a heart sensor as well as current generating circuitry wired to deliver an electrical defibrillation pulse through the electrode pad. Alternatively, the electrode can be securable directly to the upper arm region or upper leg region of the patient. In yet another alternative embodiment, the electrode can be temporarily positioned on an upper arm region or upper leg region through the use of a paddle assembly such as those commonly seen in hospital emergency rooms. The armband may also include a housing containing a heart sensor as well as current generating circuitry wired to deliver an electrical defibrillation pulse through the electrode pad.

In one embodiment, the automated external defibrillator of the present invention includes at least one armband designed for continuous wear by a patient with a known susceptibility to SCA.

In an alternative embodiment, the automated external defibrillator of the present invention includes at least one armband designed to be selectively placed by first responders or hospital personnel treating a patient suffering from SCA.

DETAILED DESCRIPTION OF THE PREFERRED EMBODIMENTS

The present invention includes systems, apparatuses, and methods for reducing the maximum discharge requirements associated with current automated external defibrillators. Generally, an automated external defibrillator includes a pair of electrodes for delivering an electrical defibrillation pulse to a patient suffering from Sudden Cardiac Arrest. As described herein, positioning at least one electrode, be it configured as an adjustable strap device, an adhesively applied electrode assembly, or a manually positioned electrode pad, on a limb proximate the torso significantly reduces the maximum discharge requirement of the automated external defibrillator through the combination of reduced transthoracic impedance as well as conduction of the electrical defibrillation pulse to the cardiac muscle through the arterial and/or veinous systems in proximity to the limb. Electrodes can be selectively placed on either the arms or legs of a patient in any appropriate position, most preferably proximate the torso of the patient.

Figure 1:
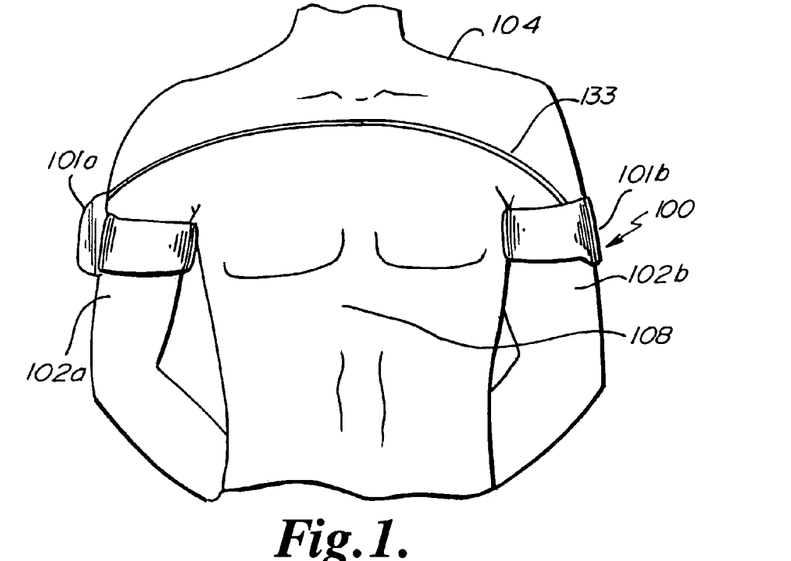
FIG. 1 is a front view of a torso including an automated external defibrillator of the present invention.
Figure 2:
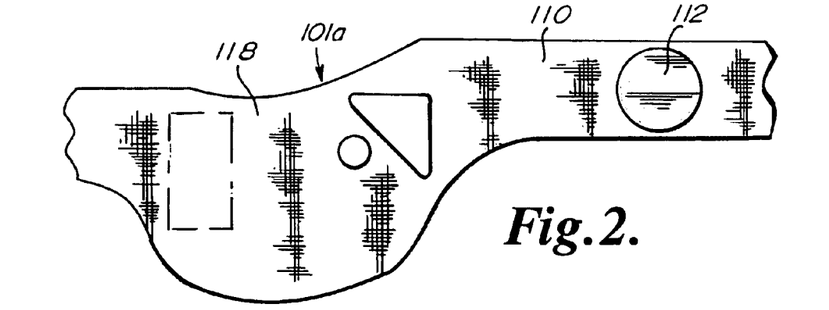
FIG. 2 is a bottom view of an embodiment of an armband device.
Figure 3:
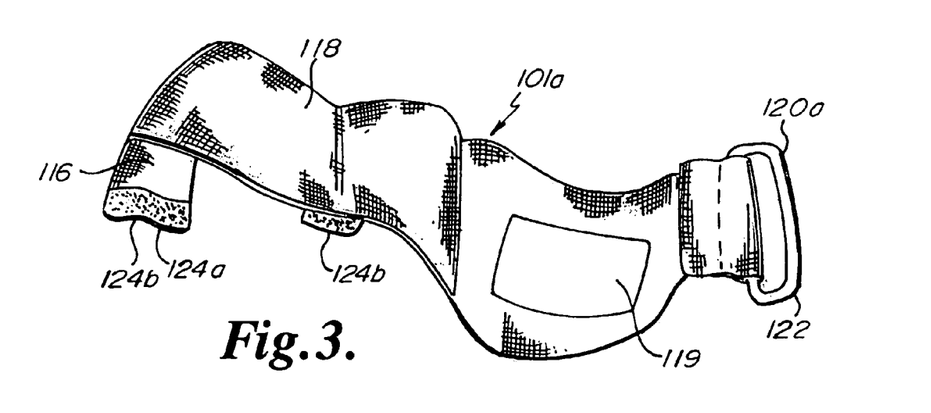
FIG. 3 is a bottom, perspective view of the armband device of FIG. 2.

As depicted in FIG. 1, an embodiment of an automated external defibrillator 100 of the present invention comprises a first adjustable strap device 101a and a second adjustable strap device 101b that are securely attached to the upper arms 102a, 102b of a human torso 104. As depicted, adjustable strap devices 101a, 101b are fixedly secured proximate the torso 104 on upper arms 102a, 102b such that they are in relatively close proximity to a chest region 108.

In its most general form as depicted in FIGS. 2, 3, 4 and 5, first adjustable strap device 101a comprises an elastic band 110, an electrode 112 and an electrical assembly 114. Elastic band 110 generally includes an exterior surface 116 and an interior surface 118. Interior surface 118 can include a bar code 119 or other label including important calibration or manufacturing data such as serial numbers, date of manufacture, date of calibration, etc. Elastic band 110 is preferably constructed of an elastic material such as Neoprene or other medically suitable elastic material. Elastic band 110 has a pair of ends 120a, 120b. In the present embodiment, end 120a includes a buckle 122 dimensioned to accommodate end 120b. Generally, elastic band 110 includes a pair of fastening members 124a, 124b, most preferably Velcro® on the exterior surface 116. Fastening member 124a is located proximate end 120b while fastening member 124b is closer to electrical assembly 114.

Electrode 112 is attached to the interior surface 118 of elastic band 110. Electrode 112 is preferably a standard multi-layer design including a conductive portion attached to lead wires as disclosed in U.S. Pat. Nos. 5,402,884; 5,579,919; 5,697,955; and 6,115,638, all of which are assigned to Cardiac Science, Inc., and hereby incorporated by reference in their entirety. Electrical assembly 114 is attached to exterior surface 116. In a preferred embodiment, electrical assembly 114 generally comprises an electrical housing 126 containing an electrical display 128, for example, a liquid crystal display, a heart sensor circuit 130 and a battery based power circuit 132.

Second adjustable strap device 101b generally resembles and is constructed similarly to first adjustable strap device 111a. Second adjustable strap device 101b includes an elastic band 110 and electrode 112 as described previously. However, second adjustable strap device 101b differs from first adjustable strap device 101a in that the electrical housing 126 including electrical display 128, heart sensor circuit 130 and power circuit 132, are not present on second adjustable strap device 101b. A lead wire 133 connects electrode 112 on second adjustable strap device 101b with electrical housing 126 on first adjustable strap device 101a.

Figure 4:
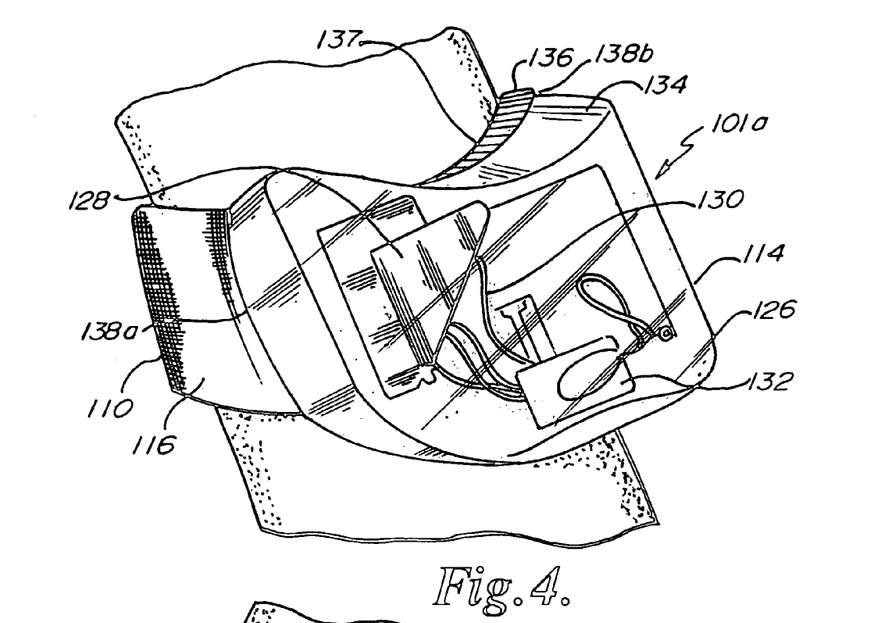
FIG. 4 is a perspective, top view of the armband device of FIG. 2.
Figure 5:
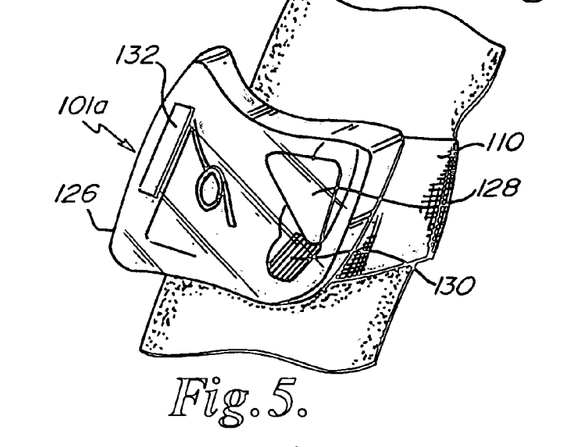
FIG. 5 is a perspective, top view of the armband device of FIG. 2.
Figure 6:
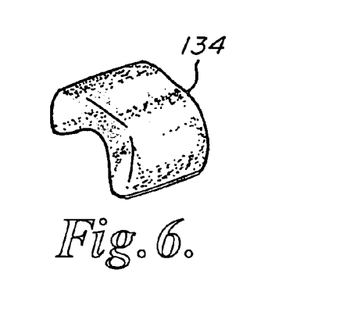
FIG. 6 is a perspective, top view of an embodiment of a top cover.
Figure 7:
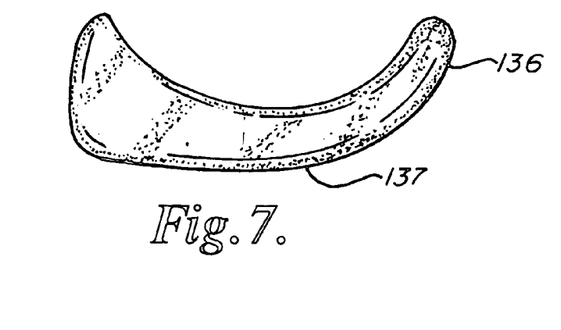
FIG. 7 is a side view of an embodiment of a bottom cover.
Figure 8:
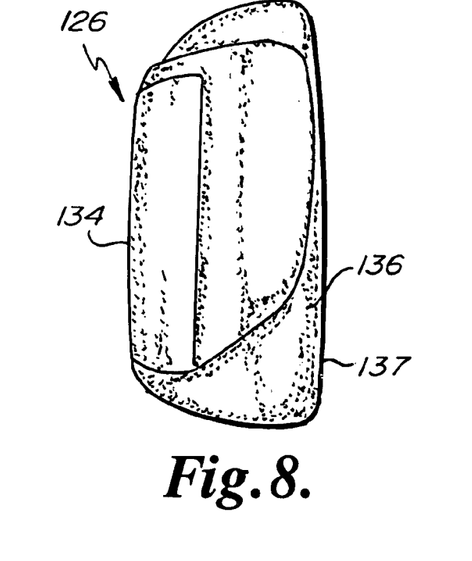
FIG. 8 is a side view of an embodiment of an electrical housing.

Depicted more clearly in FIGS. 6, 7 and 8, an embodiment of electrical housing 126 comprises a top cover 134 and a back cover 136. Top cover 134 and back cover 136 are generally molded of a polymeric material possessing material traits that exhibit water, heat, flame, impact and humidity resistance such as PETG. In a preferred embodiment, back cover 136 is molded to have a bottom surface 137 which in one orientation generally conforms to the typical rounded shape of a patient's limb. In a preferred embodiment, top cover 134 is transparent allowing internally mounted components such as electrical display 128, heart sensor 130 and power circuit 132 to be visible within electrical housing 126 as shown in FIGS. 4 and 5.

Figure 9:
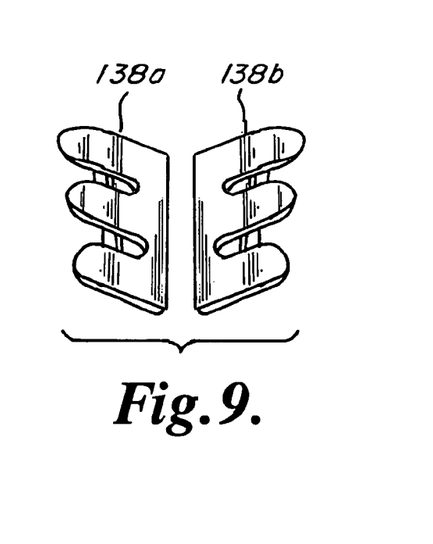
FIG. 9 is a top view of a pair of side pieces.
Figure 10:
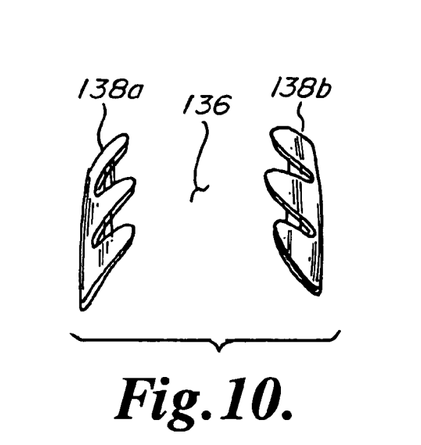
FIG. 10 is a top view of a partially assembled electrical housing.

Electrical housing 126 can also include a pair of side pieces 138*a*, 138*b*, depicted in FIGS. 9 and 10, that are attached to back cover 136. Electrical housing 126 can also include a layer of internal foam 140, depicted in FIG. 11, placed against back cover 136 to protect and support the internally mounted components. Side pieces 138*a*, 138*b* can then be operably attached to armband 110 such that back cover 136 is oriented such that it generally faces the same direction as interior surface 118.

Figure 11:
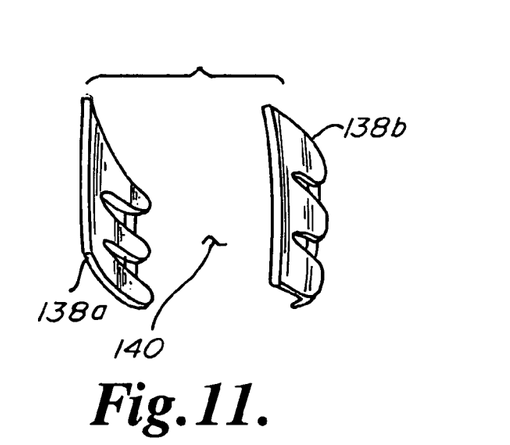
FIG. 11 is a top view of a partially assembled electrical housing.

Electrical display 128, heart sensor 130 and power circuit 132 are positioned on internal foam 140. Electrical display 128 is of the type generally well known to one skilled in the art of medical devices. Electrical display 128 typically displays the status of various components of the automated external defibrillator 100 including various battery levels and operational states as well as readings and outputs generated by the heart sensor 130 and power circuit 132. In a preferred embodiment, electrical display 128 has its own power source, for example, a button-type lithium battery.

Power circuit 132 is of the type generally well known to one skilled in the art of medical devices, for example, a circuit as disclosed and described in U.S. Pat. Nos. 5,405,361; and 5,643,324, both assigned to Cardiac Science, Inc., and hereby incorporated by reference in their entirety. The significant difference between power circuit 132 of the present invention and those described in the prior art being an ability to reduce the discharge capacity of power circuit 132 by a significant amount due to the positioning of electrode 112 on upper arm 102*a*. As is discussed later, positioning at least one electrode 112 on an upper arm 102*a*, proximate torso 104 results in a significant decrease in impedance as compared to the typical transthoracic impedance experienced with chest region 108 positioning of typical automated external defibrillators as well as utilizing conduction properties of the arterial and veinous systems to deliver the electrical defibrillation pulse to the cardiac muscle. The combination of reduced impedance and conduction through the arterial and veinous systems allows power circuit 132 to be appropriately downsized in terms of maximum electrical defibrillation pulse delivery requirements.

Heart sensor 130 is of the type generally well known to one skilled in the art of medical devices, for example, a sensor as disclosed and described in U.S. Pat. Nos. 6,289,243; 6,480,734; and 6,490,478, all of which are assigned to Cardiac Science, Inc., and hereby incorporated by reference in their entirety. Most typically, heart sensor 130 comprises hardware, software and sensors which in combination are capable of determining when a patient is experiencing SCA, distinguishing when delivery of a shocking waveform is appropriate, communicating with power circuit 132 to administer such a waveform, and monitoring the results of administering such a waveform. In addition to electrical display 128, heart sensor 130 and power circuit 132, the required wiring between these components is present within electrical housing 126. In addition, the leadwires, both those internal to first adjustable strap device 101*a* and leadwire 133 of electrode 112 are wired into power circuit 132 such that an electrical defibrillation pulse can be administered to the patient.

Once the internal components have been mounted on back cover 136, electrical housing 126 is closed by attaching top cover 134. The attachment of top cover 134 can be accomplished using fasteners such as screws or clips or through a snap-fit design in which top cover 134 and back cover 136 can be operably engaged and disengaged through hand manipulation of electrical housing 126. Regardless of which mechanism is selected for attaching front cover 134 to back cover 136, the mechanism preferably includes suitable means for removing the front cover 134 as battery replacement and other diagnostic and calibration services are generally necessary on a routine basis, for example, monthly, quarterly or semi-annually. In a preferred embodiment, heart sensor 130 and power circuit 132 are powered with a shared battery, for example a 9 volt battery. In alternative embodiments, heart sensor 130 and power circuit 132 can be separately powered using batteries, for example, a 9 volt battery and a button-type lithium battery.

Figures 12, 13, 14:
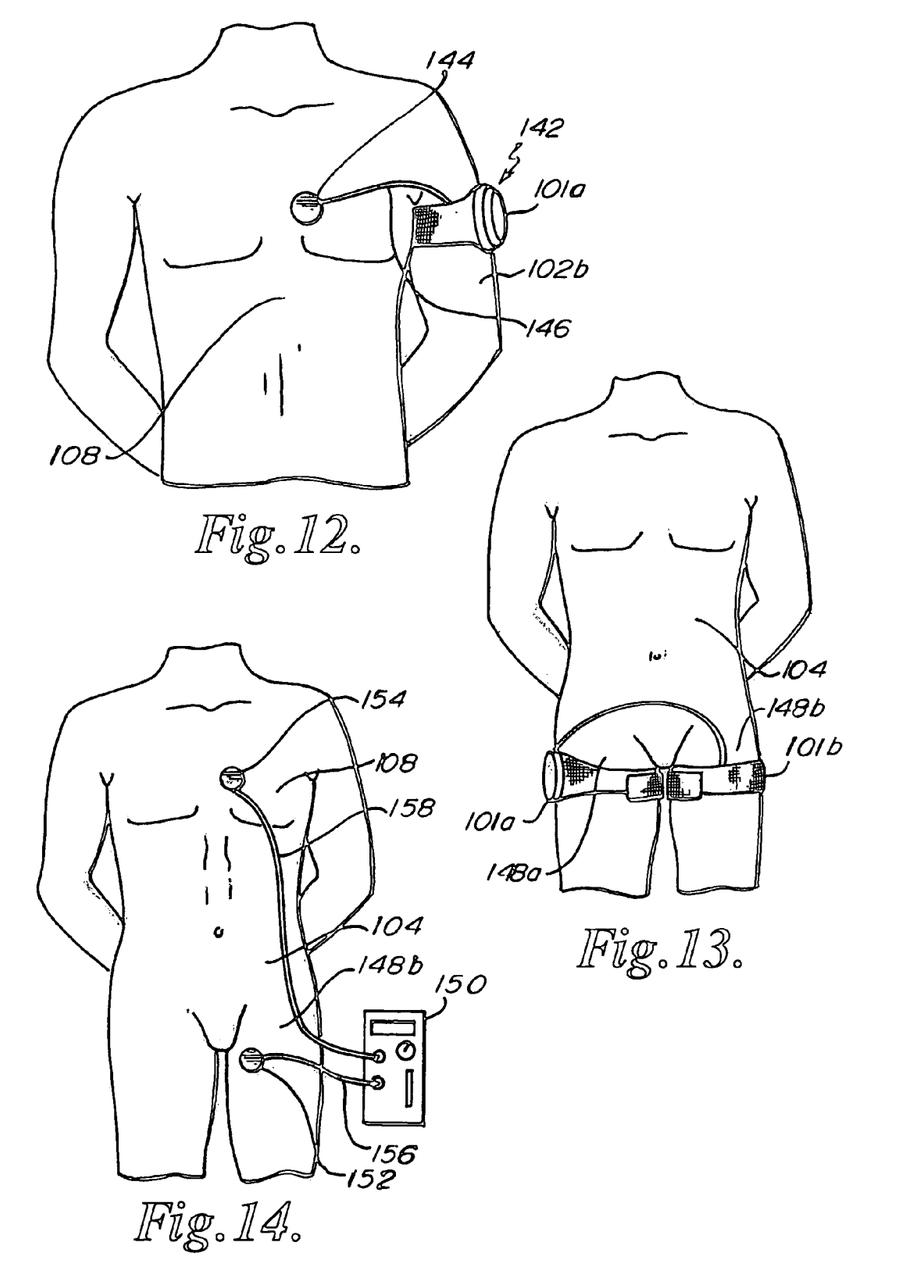
FIG. 12 is a front view of a torso including an embodiment of an automated external defibrillator of the present invention.
FIG. 13 is a front view of a torso including an embodiment of an automated external defibrillator of the present invention.
FIG. 14 is a front view of a torso including an embodiment of an automated external defibrillator of the present invention.

As depicted in FIG. 12, an alternative embodiment of the present invention includes an automated external defibrillator 142 comprising first adjustable strap device 101*a* present on upper arm 102*b* and an electrode assembly 144 located on the chest region 108. Electrode assembly 144 typically includes an adhesive backing useful in adhering the electrode assembly 144 to the chest region 108. A leadwire 146 connects electrode assembly 144 with the power circuit 132 present on first adjustable strap device 101*a*.

As depicted in FIG. 13, first adjustable strap device 101*a* and second adjustable strap device 101*b* can be configured for positioning over the upper legs 148*a*, 148*b* of a patient proximate to torso 104. Similarly, a more traditional external defibrillator 150, for example, a model Powerheart CRM manufactured by Cardiac Science, Inc., can be used to deliver an electrical defibrillation pulse by positioning a first electrode assembly 152 on an upper leg 148*b* proximate the torso 104 and a second electrode assembly 154 over the chest region 108 as shown in FIG. 14. First electrode assembly 152 includes a first leadwire assembly 156 while second electrode assembly 154 includes a second leadwire assembly 158.

Figure 15:
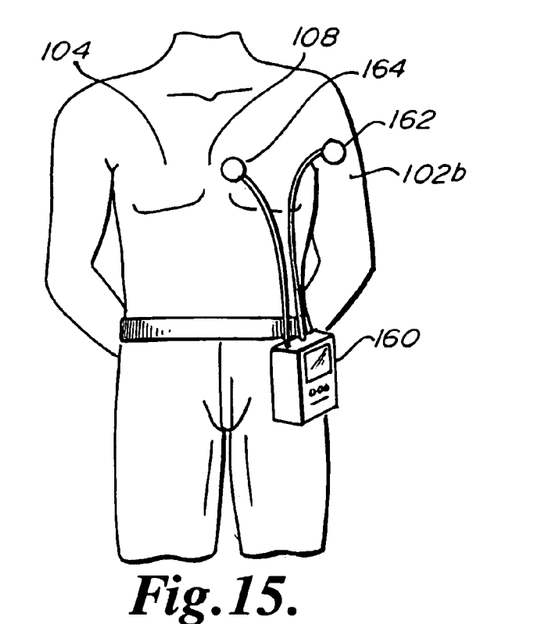
FIG. 15 is a front view of a torso including an embodiment of an automated external defibrillator of the present invention.

In another alternative embodiment shown in FIG. 15, an automatic external defibrillator 160, for example a model Powerheart AED manufactured by Cardiac Science, Inc., can be used to deliver an electrical defibrillation pulse by positioning a first electrode assembly 162 on the upper arm 102*b* and a second electrode assembly 164 over the chest region 108. First electrode assembly 162 includes a first leadwire assembly 166 and second electrode assembly 164 includes a second leadwire assembly 168.

Figure 16:
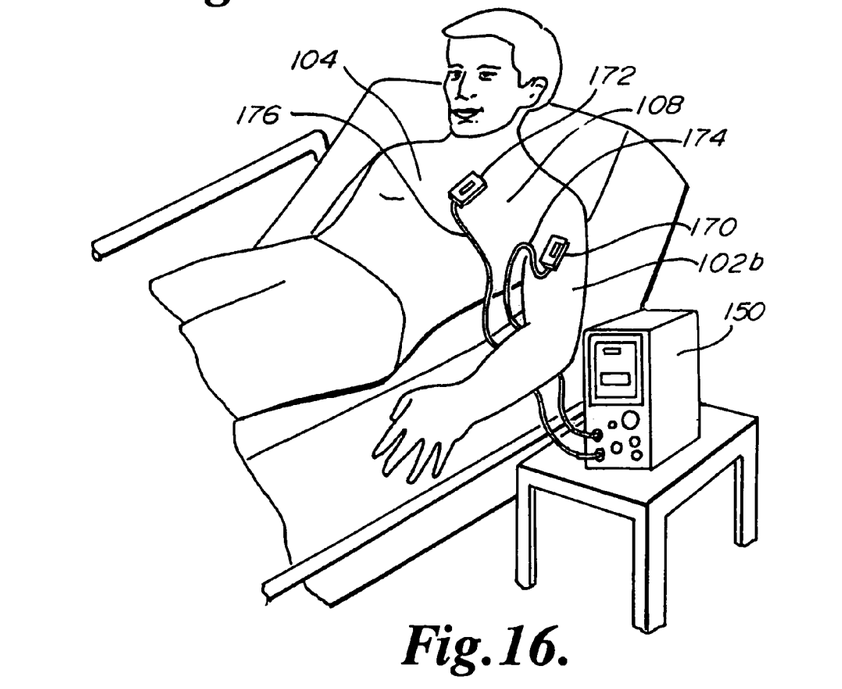
FIG. 16 is a view of bed-laden patient utilizing an embodiment of an automated external defibrillator of the present invention.

In another alternative embodiment as shown in FIG. 16, automatic external defibrillator 150 can be used with a first electrode pad 170 and a second electrode pad 172. First electrode pad 170 and second electrode pad 172 are typically hand positioned by a medical professional during a medical emergency involving a patient experiencing Sudden Cardiac Arrest. As depicted, first electrode pad 170 is positioned on upper arm 102*b* whiled second electrode pad 172 is positioned over chest region 108. First electrode pad 170 includes a first leadwire assembly 174 and second electrode pad 172 includes a second leadwire assembly 176.

It should be noted that while specific electrode configurations have been described, any suitable configurations of electrodes, wherein at least a portion of the electrical defibrillation pulse is delivered through the limb of a patient, can be used without departing from the spirit or scope of the invention.

In actual use, the automated external defibrillators of the present invention utilize at least one electrode positioned on a limb, e.g., the upper arm generally in the area of the armpit region. The impedance of the upper arms is typically a small value in comparison to transthoracic impedance of the chest region in that no air is present in the armpit region and tissue and bone thicknesses are reduced in comparison to the chest region. In addition, placement of an electrode on a limb proximate the torso results in the electrical defibrillation pulse being at least partially delivered to the cardiac muscle by conduction through the arterial and/or veinous systems in proximity to the limb. As disclosed in Table 6.16, FIG. 2.20, FIG. 2.39 and FIG. 2.40 of "Applied Bioelectricity: From Electrical Stimulation to Electropathology," authored by J. Patrick Reilly, and herein incorporated by reference in its entirety, the reduced impedance in the limbs proximate the torso results in significantly reduced ventricular fibrillation thresholds as compared to measurements strictly across the chest region. Using the significant reduction in the ventricular fibrillation threshold as measured from the limbs proximate the torso to the chest region, the automated external defibrillators of the present invention can deliver the same effective electrical defibrillation pulse to the cardiac muscle heart using power circuits having maximum electrical defibrillation pulse capacities significantly below current designs using electrodes placed exclusively across the chest region.

With regard to automated external defibrillator 100 depicted in FIG. 1, a variety of uses are possible. For example, patients with a known susceptibility to SCA or hospital patients can utilize first adjustable strap device 101a and second adjustable strap device 101b merely by positioning the elastic band 110 around upper arms 102a, 102b and sliding them in proximity to torso 104. Once first adjustable strap device 101a and second adjustable strap device 101b are properly positioned, elastic band 110 can be tightly secured by inserting end 120b through buckle 122, pulling elastic band 110 tight and securing fastening members 124a, 124b. Once first adjustable strap device 101a and second adjustable strap device 101b have been secured, heart sensor 130 begins monitoring, either automatically or by manual initiation, for signs of SCA. In the event that heart sensor 130 detects SCA and determines that administering a shocking waveform is necessary, heart sensor 130 initiates power circuit 132 to discharge such a waveform. The waveform is transmitted from the power circuit 132 through the leadwire in first adjustable strap device 101a and leadwire 133 to the electrodes 112 whereby the waveform is delivered into the upper arms 102a, 102b and subsequently to the cardiac muscle.

In the embodiment depicted in FIG. 12, automated external defibrillator 142 similarly includes first adjustable strap device 101a positioned over the upper arm 102b near torso 104. In addition, electrode 144 is positioned generally over the chest region 108. Following the positioning of first adjustable strap device 101a, heart sensor 130, either through automatic or manual initiation, begins monitoring for SCA. If heart sensor 130 detects SCA and determines that a shocking waveform should be administered, heart sensor 130 directs power circuit 132 to discharge the electrical defibrillation pulse through the leadwire present within first armband device 101a as well as leadwire 146 to electrode 112 and electrode 144.

All other defibrillator configurations described herein work similarly to that described above in that each provides for the generation of an electrical defibrillation pulse and delivery of that pulse to the limb of a patient enabling the defibrillation pulse to reach the heart and attempt to restore the heart to its normal operating condition. As such, any defibrillation configuration achieving this feat is deemed to be within the scope of this invention.

While automated external defibrillators 100 and 142 have each been described as integrally including heart sensor 130 for detecting SCA, other embodiments are envisioned in which the heart sensor 130 is a separable component. As such, automated external defibrillators 100 and 142 may include a terminal or other connector to interface with a remote heart sensor 130 through a communications wire. In other embodiments, automated external defibrillators 100 and 142 may include a wireless receiver to receive a signal transmitted from a heart sensor 130 remote from automated external defibrillators 100 and 142.

While various embodiments of the present invention have been described, it will be obvious to one skilled in the art that the invention make take other forms without departing from the spirit of the essential attributes thereof; therefore, the illustrated embodiments should be considered in all respects as illustrative and not restrictive.

What is claimed:

1. A method of delivering an electrical defibrillation pulse to the heart of a patient comprising the steps of:
    positioning a pair of electrodes on the exterior surface of the body of the patient, wherein at least one of said pair of electrodes is placed on one of the limbs of the patient in a position proximate the torso of the patient; and
    delivering an electrical defibrillation pulse through said pair electrodes, wherein the electrical defibrillation pulse is directed into the limb upon which said electrode is placed enabling the electrical defibrillation pulse to travel from the limb to the heart of the patient.

2. The method of claim 1, wherein the travel of the electrical defibrillation pulse is through an arterial or veinous system of the patient.

3. The method of claim 1, wherein each of said pair of electrodes are placed on a seperate limb of said patient in a position proximate the torso of the patient.

4. The method of claim 1, wherein said at least one electrode is placed on an upper arm region of the patient.

5. The method of claim 1, wherein said at least one electrode is placed on an upper leg region of the patient.

6. The method of claim 1, further comprising delivering a plurality of defibrillation pulses through said pair of electrodes.

7. A system for delivering an external, electrical defibrillation pulse to the heart of a patient, comprising:
    means for generating an electrical defibrillation pulse; and
    means for delivering the generated electrical defibrillation pulse to the body of the patient, wherein said means for delivering delivers said generated electrical defibrillation pulse through at least one limb of the patient enabling the delivered electrical defibrillation pulse to travel from the limb to the heart of the patient.

8. The system of claim 7, wherein the delivered electrical defibrillation pulse travels through an arterial or veinous system of the patient.

9. The system of claim 7, wherein said means for delivering comprises a pair of electrodes and wherein each of said pair of electrodes is positioned on a limb of a patient in a position proximate the torso of the patient.

10. The system of claim 7, wherein said means for delivering comprises a pair of electrodes and wherein at least one of said pair of electrodes is positioned on an upper arm region of the patient.

11. The system of claim 7, wherein said means for delivering comprises a pair of electrodes and wherein at least one of said pair of electrodes is positioned on an upper leg region of the patient.

12. A system for delivering an external, electrical defibrillation pulse to the heart of a patient, comprising:
   a power circuit, wherein said power circuit generates an electrical defibrillation pulse; and
   a pair of electrodes, wherein said pair of electrodes is operably coupled to said power circuit, wherein at least one of said pair of electrodes is placed on one of the limbs of the patient in a position proximate the torso of the patient, and wherein the electrical defibrillation pulse is directed into the limb upon which one of the electrodes is placed enabling the electrical defibrillation pulse to travel from the limb to the heart of the patient.

13. The system of claim 12, wherein the travel of the delivered electrical defibrillation pulse is through an arterial or veinous system of the patient.

14. The system of claim 12, wherein both of said pair of electrodes are placed on a limb of the patient in a position proximate the torso of a patient.

15. The system of claim 12, wherein at least one of said pair of electrodes is placed on an upper arm region of the patient.

16. The system of claim 12, wherein at least one of said pair of electrodes is placed on an upper leg region of the patient.

* * * * *